(12) United States Patent
Ye

(10) Patent No.: US 9,532,975 B2
(45) Date of Patent: Jan. 3, 2017

(54) USE OF LEVO-OXIRACETAM AND OXIRACETAM IN PREPARATION OF MEDICINES FOR PREVENTING OR TREATING COMA

(75) Inventor: Lei Ye, Chongqing (CN)

(73) Assignee: CHONGQING RUNZE PHARMACEUTICAL COMPANY LIMITED., Yubei, Chongqing (CN)

( * ) Notice: Subject to any disclaimer, the term of this patent is extended or adjusted under 35 U.S.C. 154(b) by 0 days.

(21) Appl. No.: 14/354,595

(22) PCT Filed: Apr. 24, 2012

(86) PCT No.: PCT/CN2012/074576
§ 371 (c)(1),
(2), (4) Date: Apr. 27, 2014

(87) PCT Pub. No.: WO2013/075459
PCT Pub. Date: May 30, 2013

(65) Prior Publication Data
US 2014/0275206 A1   Sep. 18, 2014

(30) Foreign Application Priority Data
Nov. 23, 2011 (CN) .......................... 2011 1 0376607

(51) Int. Cl.
*A61K 31/4015* (2006.01)

(52) U.S. Cl.
CPC ................................ *A61K 31/4015* (2013.01)

(58) Field of Classification Search
CPC .................................................. A61K 31/4015
See application file for complete search history.

(56) References Cited

FOREIGN PATENT DOCUMENTS

WO    WO 2011120281 A1 * 10/2011

OTHER PUBLICATIONS

Lyon, "Reversal of Alcoholic Coma by Naloxone", Ann Intern Med. 1982;96(4):464-465.*
Shi-Lei, "Effect of naloxone on cognitive function in vascular dementia in rats", Indian J Med Res. Jun. 2002;115:265-71.*
Pepeu, "Nootropic Drugs and Brain Cholinergic Mechanisms", Progress in Neuro-Psychopharmacology and Biological Psychiatry, 1989, 13, pp. 77-88.*

* cited by examiner

*Primary Examiner* — Sahar Javanmard

(57) ABSTRACT

The present invention is to provide uses of the L-oxiracetam in preparation of medicines for preventing or treating coma. Experimental results show that L-oxiracetam wake-promoting effects of alcoholism-induced coma is obvious, and D-oxiracetam has basically no effect. The effect of the above wake-promoting effects of L-oxiracetam is 2 times greater than racemic oxiracetam. The wake-promoting effects of L-oxiracetam on trauma or anesthesia-induced coma are both significant.

7 Claims, No Drawings

USE OF LEVO-OXIRACETAM AND OXIRACETAM IN PREPARATION OF MEDICINES FOR PREVENTING OR TREATING COMA

BACKGROUND OF THE INVENTION

1. Field of Invention

The present invention relates to medical uses of the levo-oxiracetam and oxiracetam, particularly to use of levo-oxiracetam and oxiracetam in preparation of medicines for preventing or treating coma.

2. Description of the Related Art

Oxiracetam (oxiracetam), is a nootropic drug that first synthesized in 1974 by the Italian pharmaceutical company, ISF S.P.A., the drug get into the Italian market in 1987. Oxiracetam is a racemic composition including two isomers (S)-oxiracetam and (R)-oxiracetam. Reports about oxiracetam shows that oxiracetam, which can promote brain ATP, promote synthesis of acetylcholine, enhances nerve conduction, hypoxia-induced retrograde amnesia improvement effect and memory, and improve learning ability, is the treatment of Alzheimer-type dementia (AD), vascular dementia (VD), etc. disorders of effective drugs.

L-oxiracetam ((S)-4-hydroxy-2-oxo-pyrrolidineacetamide) is of levo type of oxiracetam (CAS 62613-82-5), white microcrystalline powder with melting point at 135-136° C. and optical rotation of −36.0° (C=1.00 in water). The solubility of L-oxiracetam is significantly better than the racemate. There is no reports indicates that L-oxiracetam currently is used as a single drug.

CN 101367757A discloses a preparation method of (S)-4-hydroxy-2-oxo-1-pyrrolidineacetamide preparation. It uses (S)-4-halo-3-hydroxybutyric acid ester as a raw material in a polar solvent and under basic conditions to produce L-oxiracetam. The basic conditions means that the reaction is carried through increasing alkali in the course of the reaction, and dropping chlorides to control the pH value. The crude product obtained by using the cation exchange resin is an acidic aqueous solution of the product, and then using an anion exchange resin to neutralize the acidic solution, and the neutralized solution was concentrated to get the crude product and the crude product was recrystallized by ethanol once with methanol/acetone mixed solvent of crystallization or recrystallization from isopropanol once a process for preparing L-oxiracetam.

Coma is the most serious disturbance of consciousness due to the high suppression of lower cortical and subcortical reticular structure, that is, a sustained interruption or most highly suppressed state of complete loss of consciousness of the highest nervous activities, and a serious condition in patients with complete loss of consciousness. Alcoholism is one of three causes of coma. With the accelerated pace of modem life and people's increasing mental stress, alcoholics increasingly appeared, the phenomena of being drunk and alcohol coma are increasingly more common Trauma-induced coma is one of the three causes of coma occurred today in a car accident, falls and other trauma-induced coma and is also more common Anesthesia-induced coma for today is a common medical malpractice. Some patients could not wake up and no perception after anesthesia. Anesthesia-induced coma is one of the three causes of coma. How to further improve the cure rate awaking coma to reduce mortality and improve the level of arousal and cognitive function is a major issue facing today, to solve this problem would have important practical significance.

SUMMARY OF THE INVENTION

The object of the present invention is to provide use of oxiracetam and L-oxiracetam in the pharmaceutical field, specifically to provide a use of levo-oxiracetam and oxiracetam in preparation of medicines for preventing or treating coma.

Specifically, the present invention relates to the preparation of L-oxiracetam for prevention or treatment of alcoholism as an induced coma medicament, narcotic-induced coma medicament and traumatic coma medicament. The present invention relates to the preparation of oxiracetam for prevention or treatment of alcoholism as an induced coma medicament, narcotic-induced coma medicament and traumatic coma medicament.

The use of levo-oxiracetam and oxiracetam in preparation of medicines for preventing or treating coma is specifically referred to the preparation of the pharmaceutical composition of active ingredients as oxiracetam or L-oxiracetam. The dosage forms can be injections such as powder for injection or injection solution, or can be oral formulations such as tablets, pills, powders, granules, capsules and the like. The formulations described above can be prepared according to conventional methods. Said dosage forms are preferably as oral capsules, tablets or injections.

The dosage of oral formulations of L-oxiracetam described above is 5-30 mg/kg/day, more preferably 10-20 mg/kg/day. The dosage of injection of L-oxiracetam is 50-90 mg/kg/times. The dosage of oral formulations of L-oxiracetam described above is 10-60 mg/kg/day, and more preferably is 20-40 mg/kg/day. The dosage of injection of oxiracetam is 50-90 mg/kg/times.100-180 mg/kg/times.

Most preferably, the use of levo-oxiracetam and oxiracetam in preparation of medicines for preventing or treating coma utilize 99.3% purity (optical purity) of L-oxiracetam as an active ingredient, based on the weight percentage.

To further verifying the pharmaceutical effect of the present invention, the inventors have conducted the following tests.

A. The Pharmacokinetics of L-Oxiracetam In Vivo and Studies of Absolute Bioavailability The study of comparing the pharmacokinetic of the racemic oxiracetam and L-oxiracetam determines the dose orally and intravenously to Beagle dogs for 50 mg/kg.

Take six adult Beagle dogs, the numbers of female and male were equal, which were weighted 10.0±0.5 kg and randomly divided into three groups, and each group were two with same numbers of the male and female. Latin square crossover method was used (see Table 1). Beagle dogs were administered orally and intravenously at a dose of 50 mg/kg. L-oxiracetam samples with 99.3% (optically pure) of purity were used. Each route of administration was performed every week. Animals orally administered were fasted for 12 hours after administration, then continued fasting three hours after administration. Blank blood was taken prior to administration. Blood sample were taken 1 mL from forelimbs vein into heparinized tubes in 0.083, 0.25, 0.5, 0.75, 1.0, 1.5, 2.0, 4.0, 6.0, 8.0, 12.0 and 24.0 hours after oral administration, or taken in 0.083, 0.25, 0.5, 0.75, 1.0, 1.5, 2.0, 4.0, 6.0, 8.0, 12.0 and 24.0 hours after intravenous administration, and centrifuged to obtain plasma. The concentrations of drugs in plasma were determined by LC-MS-MS method. The results in the table below 2-7.

TABLE 1

Experimental design of Latin square crossover three-cycle for Beagle dogs grouping

| | ORT, p.o | | s-ORT, p.o | | sORT, i.v | |
|---|---|---|---|---|---|---|
| Gender | ♀ | ♂ | ♀ | ♂ | ♀ | ♂ |
| First cycle | 1 | 4 | 2 | 5 | 3 | 6 |
| Second Cycle | 3 | 6 | 1 | 4 | 2 | 5 |
| Third cycle | 2 | 5 | 3 | 6 | 1 | 4 |

Note:
ORT is Oxiracetam; s-ORT is levo oxiracetam

The drug concentrations in plasma of dogs administrated 50 mg/kg of oxiracetam and L-oxiracetam intravenously and orally are listed in Table 2-4.

TABLE 2

Drug concentrations in plasma of Beagle dogs after administrated intravenously 50 mg/kg of oxiracetam and L-oxiracetam (μg/mL)

| Time (h) | 1 | 2 | 3 | 4 | 5 | 6 | $\overline{X}$ | s |
|---|---|---|---|---|---|---|---|---|
| 0.083333333 | 20.80 | ND | 19.80 | ND | 2.12 | 0.70 | 10.86 | 10.927932 |
| 0.25 | 18.50 | 4.02 | 20.90 | 4.02 | 3.19 | 11.10 | 10.29 | 7.8697914 |
| 0.5 | 19.90 | 12.60 | 23.30 | 22.00 | 7.52 | 19.90 | 17.54 | 6.1483711 |
| 0.75 | 17.20 | 28.70 | 38.80 | 36.70 | 15.00 | 28.80 | 27.53 | 9.7754113 |
| 1 | 30.80 | 35.30 | 43.40 | 45.60 | 23.30 | 40.20 | 36.43 | 8.3934895 |
| 1.5 | 38.80 | 34.50 | 39.30 | 45.00 | 27.30 | 47.60 | 38.75 | 7.3055458 |
| 2 | 35.30 | 31.00 | 32.60 | 39.40 | 22.20 | 41.00 | 33.58 | 6.7676929 |
| 4 | 13.00 | 14.30 | 11.10 | 14.70 | 9.37 | 13.40 | 12.65 | 2.0381732 |
| 6 | 9.35 | Abortion | 6.49 | 9.00 | 6.50 | 6.57 | 7.58 | 1.4597842 |
| 8 | 3.95 | 3.56 | 3.93 | 5.43 | 8.10 | 4.14 | 4.85 | 1.7160118 |
| 12 | 1.51 | 1.27 | 1.46 | 2.56 | 2.74 | 2.15 | 1.95 | 0.6216564 |
| 24 | 0.05 | 0.05 | 0.64 | 1.18 | ND | ND | 0.48 | 0.54 |

ND: Less than 0.5 μg/mL

TABLE 3

Drug concentrations in plasma of Beagle dogs after fed orally 50 mg/kg L-oxiracetam (μg/mL)

| Time (h) | 1 | 2 | 3 | 4 | 5 | 6 | $\overline{X}$ | s |
|---|---|---|---|---|---|---|---|---|
| 0.083333333 | ND | ND | 42.00 | ND | ND | 21.90 | 31.95 | 14.21 |
| 0.25 | 1.51 | 38.50 | 39.60 | 1.42 | 1.17 | 31.50 | 18.95 | 19.46 |
| 0.5 | 10.30 | 23.90 | 42.20 | 10.60 | 5.52 | 31.30 | 20.64 | 14.32 |
| 0.75 | 27.50 | 5.45 | 52.60 | 17.00 | 17.30 | 43.20 | 27.18 | 17.76 |
| 1 | 24.70 | 46.60 | 48.40 | 27.00 | 34.00 | 42.90 | 37.27 | 10.17 |
| 1.5 | 26.30 | 52.10 | 46.70 | 27.60 | 44.30 | 41.50 | 39.75 | 10.52 |
| 2 | 23.00 | 39.10 | 36.50 | 21.60 | 44.70 | 37.10 | 33.67 | 9.28 |
| 4 | 12.40 | 14.00 | 13.70 | 9.80 | 15.80 | 13.60 | 13.22 | 2.00 |
| 6 | 4.09 | 8.92 | 4.76 | 4.85 | 8.72 | 5.31 | 6.11 | 2.14 |
| 8 | 2.33 | 6.55 | 2.56 | 3.34 | 4.47 | 2.81 | 3.68 | 1.60 |
| 12 | 1.07 | 2.01 | 1.01 | 4.60 | 1.48 | 1.15 | 1.89 | 1.38 |
| 24 | ND | ND | ND | 1.47 | ND | ND | 1.47 | ND |

ND: Less than 0.5 μg/mL

TABLE 4

Drug concentrations in plasma of Beagle dogs after administrated intravenously 50 mg/kg L-oxiracetam(μg/mL)

| Time (h) | 1 | 2 | 3 | 4 | 5 | 6 | $\overline{X}$ | s |
|---|---|---|---|---|---|---|---|---|
| 0.083333333 | 117.20 | 160.60 | 107.00 | 127.00 | 150.40 | 132.60 | 132.47 | 20.12 |
| 0.25 | 156.00 | 198.00 | 78.40 | 105.00 | 124.20 | 85.80 | 124.57 | 45.60 |
| 0.5 | 94.10 | 89.10 | 99.80 | 92.90 | 94.60 | 94.50 | 94.17 | 3.44 |
| 0.75 | 64.70 | 85.70 | 77.80 | 74.80 | 77.30 | 70.00 | 75.05 | 7.19 |
| 1 | 51.00 | 72.50 | 65.40 | 60.60 | 66.20 | 60.80 | 62.75 | 7.22 |
| 1.5 | 37.00 | 51.20 | 50.60 | 43.40 | 49.00 | 74.20 | 50.90 | 12.62 |
| 2 | 26.40 | 38.90 | 69.80 | 33.20 | 36.60 | 32.00 | 39.48 | 15.46 |
| 4 | 9.13 | 13.90 | 9.33 | 11.60 | 13.30 | 24.10 | 13.56 | 5.53 |
| 6 | 3.79 | 4.88 | 5.03 | 4.97 | 5.99 | 24.90 | 8.26 | 8.18 |
| 8 | 1.79 | 2.65 | 2.19 | 2.73 | 2.75 | 2.28 | 2.40 | 0.38 |
| 12 | 0.82 | 1.18 | 0.64 | 0.92 | 1.11 | 0.75 | 0.90 | 0.21 |
| 24 | ND | ND | ND | ND | ND | ND | ND | ND |

ND: Less than 0.5 μg/mL

TABLE 5

Pharmacokinetic parameters of Beagle dogs after perfused 50 mg/kg L-oxiracetam (μg/mL)

| Statistical moment parameters | No. 1 | No. 2 | No. 3 | No. 4 | No. 5 | No. 6 | Average | Standard deviation | Minimum value | Maximum value |
|---|---|---|---|---|---|---|---|---|---|---|
| Tmax (h) | 1.50 | 1.00 | 1.00 | 1.00 | 1.50 | 1.50 | 1.25 | 0.27 | 1.00 | 1.50 |
| Cmax (mg/L) | 38.80 | 35.30 | 43.40 | 45.60 | 27.30 | 47.60 | 39.67 | 7.55 | 27.30 | 47.60 |
| AUC(0-tn) (mg/L*h) | 159.73 | 148.16 | 161.50 | 195.78 | 118.22 | 161.36 | 157.46 | 25.03 | 118.22 | 195.78 |
| AUC(0-∞) (mg/L*h) | 159.90 | 148.34 | 166.74 | 207.03 | 137.18 | 171.07 | 165.04 | 24.02 | 137.18 | 207.03 |
| MRT(0-∞) (h) | 3.77 | 3.66 | 4.80 | 6.32 | 6.27 | 3.85 | 4.78 | 1.24 | 3.66 | 6.32 |
| CL(L/h/kg) | 0.31 | 0.34 | 0.30 | 0.24 | 0.36 | 0.29 | 0.31 | 0.04 | 0.24 | 0.36 |

TABLE 6

Pharmacokinetic parameters of Beagle dogs after fed orally 50 mg/kg L-oxiracetam (μg/mL)

| Statistical moment parameters | No. 1 | No. 2 | No. 3 | No. 4 | No. 5 | No. 6 | Average | Standard deviation | Minimum value | Maximum value |
|---|---|---|---|---|---|---|---|---|---|---|
| Tmax (h) | 0.75 | 1.50 | 0.75 | 1.50 | 2.00 | 0.75 | 1.21 | 0.53 | 0.75 | 2.00 |
| Cmax (mg/L) | 27.5 | 52.10 | 52.60 | 27.60 | 44.70 | 43.20 | 41.28 | 11.29 | 27.50 | 52.60 |
| AUC(0-tn) (mg/L*h) | 103.10 | 178.87 | 170.95 | 143.12 | 162.18 | 159.69 | 152.98 | 27.23 | 103.10 | 178.87 |
| AUC(0-∞) (mg/L*h) | 106.77 | 187.21 | 174.16 | 166.96 | 167.17 | 163.52 | 160.97 | 27.86 | 106.77 | 187.21 |
| MRT(0-∞) (h) | 3.56 | 3.85 | 2.66 | 11.49 | 3.66 | 2.94 | 4.69 | 3.36 | 2.66 | 11.49 |
| CL(L/h/kg) | 0.47 | 0.27 | 0.29 | 0.30 | 0.30 | 0.31 | 0.32 | 0.07 | 0.27 | 0.47 |

TABLE 7

Pharmacokinetic parameters of Beagle dogs after administrated intravenously 50 mg/kg L-oxiracetam (μg/mL)

| Statistical moment parameters | No. 1 | No. 2 | No. 3 | No. 4 | No. 5 | No. 6 | Average | Standard deviation | Minimum value | Maximum value |
|---|---|---|---|---|---|---|---|---|---|---|
| AUC(0-tn) (mg/L*h) | 190.41 | 254.39 | 260.14 | 214.36 | 238.36 | 298.64 | 242.72 | 37.75 | 190.41 | 298.64 |
| AUC(0-∞) (mg/L*h) | 193.19 | 258.38 | 262.01 | 217.34 | 241.97 | 300.20 | 245.52 | 37.34 | 193.19 | 300.20 |
| MRT(0-∞) (h) | 1.92 | 2.03 | 1.91 | 2.10 | 2.12 | 2.58 | 2.11 | 0.25 | 1.91 | 2.58 |
| Absolute biocompatibility | 55.27% | 72.46% | 66.47% | 76.82% | 69.08% | 54.47% | 65.76% | 9.12% | 54.47% | 76.82% |

It can be known that, AUC0-∞ was 165.04±24.02 h, clearance was 0.31±0.04 L/h/kg, peak time and peak concentration was 1.25±0.27 h and 39.67±7.55·g/mL respectively of Beagle dogs after fed orally 50 mg/kg Oxiracetam. AUC0-∞ was 160.97±27.86 h, peak time and peak concentration was 1.21±0.53 h and 41.28±11.29·g/mL respectively of Beagle dogs after fed orally 50 mg/kg L-oxiracetam; absolute bioavailability estimated through AUC0-∞ was 242.72±37.75 h after intravenous administration was 65.76±9.12%.

It can be concluded that, L-oxiracetam reserved the properties of pharmacokinetic parameters of the original oxiracetam.

B. Toxicology Tests

To compare the ICR mice toxicity of L-oxiracetam and oxiracetam under GLP experimental conditions, the dose is set to 5 g/kg and prepared with a 0.5% CMC solution. Each group has 20 animals with same numbers of the male and female fed orally. The results shows two groups of animals was normal, and no significant toxicity observed continuously for 14 days without an animal deaths occurred between the two groups and had no significant difference in toxicity. Description of L-oxiracetam is not increased efficacy while increasing toxicity.

Oxiracetam is commercially available and its pharmacokinetics, toxicology and other properties are common knowledge.

C. The experimental Study of Oxiraceta, L-Oxiracetam and D-Oxiracetam Oxiracetam on the Impact of Alcohol-Induced Coma in Mice (A) Materials 1. Drugs and reagents: L-Oxiracetam, D-Oxiracetam and racemic oxiracetam; naloxone, purchased from Chongqing Yaoyou Pharmaceutical Co., Ltd.; anhydrous ethanol, purchased from Shanghai Chemical Reagent Co., Ltd. Physiological saline is commercially available. Each solution was freshly prepared.
2. Preparation of ethanol solution: anhydrous ethanol was diluted with saline to produce 30% ethanol solution, freshly prepared.
3. Experimental animals: Male mice weighing 18-22 grams were provided by the special committee, Sichuan experimental animal farms (License: SCXK (Chuan) 2008-14). Animal experiments facilities continue to maintain barriers environmental standards. Control of key environmental indicators: the temperature of 20.0-25.0° C., relative humidity of 40-70%. 10-20 air changes/hour, lighting: dark=14 h:10 h. Animals were housed in standard boxes, each box had 5.

(B) Experimental Methods

1. Preparation of alcoholic coma mouse model: With reference to the literature [1] (M. E L Yacoubi, C. Ledent, M. parmentier, et al Caffeine reduces hypnotic effects of alcohol through adenosine A2A receptor blockade [J] Neuropharmacology, 2003, 45(7):977-985) modeled the process of 30% ethanol solution intraperitoneally (0.2 ml/10 g).
2. Method of determination of states of consciousness of mouse discriminating: According to the literature [2] (Jeffrey R. Stephens, Rene H. Levy. Effects of valproate and citrulline on ammonium-Induced encephalopathy [J] Epilepsia, 1994,35 (1):164-171) performed the determination of states of consciousness: level 1, reduced activity in the cage; level 2, limb ataxia associated with reduced activity; level 3, scrolled when placed in the bottom of the back of the cage (righting reflex), but could not stand; level 4, back into the cage end position cannot be corrected, but the damage manifested as physical stimulation retraction; level 5, righting reflex (Loss of Righting Reflex, LORR) and the lack of response to noxious stimuli. Level 4, 5, considered animal in a coma.
3. Experimental Groups and Design The 150 animals were randomly divided into 10 groups: model control group (saline only); racemic Oxiracetam set up three groups, namely: 60,180,360 mg/kg group; dextral Oxiracetam up two groups, respectively: 90,180 mg/kg group; L oxiracetam set up three groups, namely: 30 mg/kg, 90 mg/kg and 180 mg/kg group; naloxone group, a dose of 1.5mg/kg. After each group were successfully prepared animal models, random tables grouped righting reflex one minute after tail vein injection. The mice were observed duration of righting reflex, that sleep time. Statistical results:

the experimental data with x±sd, said comparison between the groups were analyzed using ANOVA and q test, test level: α=0.05.

(C) Results

After administration of the sleep time of mice in each group are shown in Table 8:

| Groups | Dose (mg/kg) | Number of animals (Number) | Weight (g) | Time of Sleep (The duration of reflex action, min) |
|---|---|---|---|---|
| L-Oxiracetam | 30 | 15 | 19.6 ± 1.1 | 85.8 ± 10.6* |
|  | 75 | 15 | 19.5 ± 1.0 | 63.5 ± 9.8** |
|  | 180 | 15 | 19.5 ± 1.1 | 48.5 ± 9.1** |
| D-Oxiracetam | 30 | 15 | 19.8 ± 1.3 | 105.3 ± 15.8 |
|  | 180 | 15 | 19.3 ± 1.2 | 98.8 ± 11.6 |
| Racemic Oxiracetam | 60 | 15 | 19.2 ± 1.1 | 96.8 ± 12.7 |
|  | 150 | 15 | 19.5 ± 1.2 | 86.1 ± 9.4* |
|  | 360 | 15 | 19.4 ± 1.3 | 65.1 ± 10.2** |
| Naloxone | 1.5 | 15 | 19.3 ± 1.0 | 60.5 ± 7.8** |
| Saline | 0.1 mo/10 g | 15 | 19.7 ± 1.3 | 116.6 ± 10.1 |

From the above results, the effects of L-oxiracetam of wake-promoting on alcoholism-induced coma obvious. D-oxiracetam basically had no effect. Racemic Oxiracetam had certain awaking effect on coma due to alcoholism. The effect of L-oxiracetam of awaking about racemic oxiracetam 2 times.

(D) The Study of Ketamine-Induced Coma and Wake Experiments of 3oxiracetam, L-Oxiracetam and D-Oxiracetam in Mice.

Because of ketamine sedation, forgotten, analgesic and anesthetic properties, typical anesthetic is widely used in clinical practice, but found that ketamine sedation is too deep and too long duration, often caused by delayed recovery or has not regained consciousness, leading to potential life-threatening. For delayed recovery or not waking up, wake drugs are commonly used in clinical naloxone, studied mice induced by the ketamine coma wake role of L-oxiracetam etc.

1. Materials and Methods
1.1 Experimental animal and grouped 150 Kunming mice, male, weight (25.3±1.9) g, provided by the special committee of Sichuan experimental animal farms. (License: SCXK (Chuan) 2008-14). Animal experiments facilities continue to maintain barriers environmental standards. Control of key environmental indicators: the temperature of 20.0-25.0° C., relative humidity of 40-70%. 10-20 air changes/hour, lighting:dark=14 h:10 h. Animals were housed in standard boxes, each box 5.

After 120 mg/kg of intraperitoneal injection with ketamine-induced coma, 120 successful-modeled mice were selected randomized block design stratified into 10 groups (n=12): L oxiracetam 30,75,180 mg/kg three group; dextral Oxiracetam 30,180 mg/kg two groups; mixed spin Oxiracetam 60,150,360 mg/kg three groups; naloxone 1.5 mg/kg group; saline group (NS group).

1.2 Reagents: L-oxiracetam (according to the patent application CN 101367757A preparation), D-oxiracetam (commercially available product, batch number: 20100205) and racemic oxiracetam (commercially available product, batch number: 20100105); naloxone hydrochloride injection 1 ml: 0.4mg (Chongqing Yaoyou pharmaceutical Co., Ltd., batch number 1001020); ketamine hydrochloride injection 2 ml: 0.1 g (Henry Co., Ltd., Jiangsu Province, batch KH091201).

1.3 Experimental methods and Measurements: the mice were administrated by intraperitoneal injection of ketamine 120 mg/kg, to be righting reflex disappears after 1 min, each group were injected with L-oxiracetam 30, 75, 180 mg/kg; dextral Olathe Tan 30, 180 mg/kg; mixed spin Oxiracetam 60, 150, 360 mg/kg and naloxone 1.5 mg/kg and normal saline 10 ml/kg, mice were observed for the duration of righting reflex (recovery time). Mice after three consecutive supine standing for 5 s can not be restored righting reflex recovery after three consecutive sit-stand for the righting reflex.

1.4 Statistical analysis of data with x±sd was expressed using statistical software SPSS 12.0 for data analysis. The groups were compared using ANOVA, test level: A=0 05.

2. Results

Effect of L-oxiracetam, D-oxiracetam and racemic oxiracetam of duration of ketamine-induced coma of mice are shown in Table 9.

TABLE 9

L-oxiracetam, D-oxiracetam and racemic oxiracetam of duration of ketamine-induced coma in mice

| Groups | Dose (mg/kg) | Number of animals (Number) | Weight (g) | Time of Sleep (The duration of reflex action, min) |
|---|---|---|---|---|
| L-Oxiracetam | 30 | 12 | 19.2 ± 1.5 | 19.6 ± 5.6* |
|  | 75 | 12 | 20.6 ± 1.1 | 15.2 ± 4.9** |
|  | 180 | 12 | 19.9 ± 1.3 | 13.8 ± 3.8** |
| D-Oxiracetam | 30 | 12 | 20.5 ± 1.2 | 25.6 ± 8.9 |
|  | 180 | 12 | 19.8 ± 1.3 | 22.8 ± 6.5 |
| Racemic Oxiracetam | 60 | 12 | 20.4 ± 1.2 | 21.3 ± 6.7 |
|  | 150 | 12 | 19.8 ± 1.3 | 15.3 ± 6.4* |
|  | 360 | 12 | 19.6 ± 1.3 | 14.2 ± 6.2** |
| Naloxone | 1.5 | 12 | 20.2 ± 1.1 | 13.5 ± 4.2** |
| Saline | 0.1 mo/10 g | 12 | 20.3 ± 1.4 | 23.5 ± 5.5 |

The table above shows that L-oxiracetam had a significant awaking effect in the dose range 30-180 mg/kg. Racemic oxiracetam also had such effect in the dose range 150-360 mg/kg. D-oxiracetam with the same dose as L-oxiracetam had no effect. Positive reference drug, naloxone, also showed a significant effect on coma mice.

(E) Study of L-Oxiracetam on Promoting-Awaking Experiments in Rats with Traumatic Brain Awake Coma 1. Materials
1.1 Reagents and Drugs L-oxiracetam (prepared based on patent CN101367757A); Naloxone Hydrochloride Injection 1 ml: 0.4 mg (Chongqing Yaoyou Pharmaceutical Co., Ltd., batch number 1001020)

2. Methods
2.1 Animal Model Building, Grouping Administration

Animal experiments using 50 SD rats of clean grade, male, experiment weighing 350~400 g, purchased from Daping Hospital, Third Military Medical University Experimental Animal Center, the production license: SLXK (Chongqing) 2007-0005. Animal experiments facilities continue to maintain barriers environmental standards. Control of key environmental indicators: the temperature of 20.0-25.0° C., relative humidity of 40-70%. 10-20 air changes/hour, lighting:dark=14 h:10 h. Animals were housed in standard boxes, each box 5.

2.2 Animal Model

The model of traumatic brain coma was established with reference to the Feeney method an experimental rat model of severe traumatic brain injury in rat was established reference Feeney method. Experimental force was used as 6000 g/cm [i.e. weight of impactors (g)×falling distance of impactors (cm)]. To be shallow chloral hydrate anesthesia, parietal hair was removed and disinfected. The rats were fixed on stereotactic, craniotomy incision to the right of the dental drill in the coronal suture and sagittal suture 3 mm and 3 mm drill intersection expanded bone window to 6 mm×6 mm (the front is to the coronal suture, the left boundary is at 2 mm of the right side of the sagittal suture). The intact dura was remained. 30 g of the heavy blow cylindrical rod (strike end diameter 4 5 mm) vertical fixed stereotactic inner sleeve on the height from 20 cm to release combat site is drilling point; blow after topical hemostatic gelatin sponge, to no active bleeding after suturing the scalp. After modeling is not deep coma and removed immediately dead animals, animal unconscious selected more than 10 minutes.

2.3 Grouping and Administration 30 animals were selected after the blow caused a coma and randomly divided into three groups of 10 each. One of them is used as a control group with given 0.5 ml/100 g of saline. The second group was given 125 mg/kg of L-oxiracetam. The third group was given 1 mg/kg of naloxone hydrochloride injection. Each group in a coma for 10 minutes was administrated, then lied in rear cage quietly. Animals were observed in a coma at 1, 2, 4, 8 hours after administration, and then pressed score to grade scoring.

2.4 Coma Classification Method in Rats

Level 1: active in the cage as usual
Level 2: Reduced activity in the cage
Level 3: Reduce activity and movement disorders in the cage
Level 4: scrolling when back at the bottom of the cage (righting reflex exists) but not standing
Level 5: disappearance righting reflex but the reaction to painful stimuli limb retraction
Level 6: disappearance of righting reflex, no response to painful stimuli, disappearance of ear flaps reflex, corneal reflex, and tail squeezes not elicit escape reactions.

Level 5 and 6 are considered to be a coma.

3. Results

L-Oxiracetam in rats with traumatic brain coma role shows in Table 10.

is also showing a good wake-promoting effect, the desired effect, and clinical application of these results coincide.

DETAILED DESCRIPTION OF THE INVENTION

The following description are several embodiments of the present invention, but the present invention is not limited thereto.

EXAMPLE 1

Raw material composition:

| (a) L-oxiracetam (99.5% of purity) | 200 mg/tablet |
| (b) Lactose | 80 mg/tablet |
| (c) Microcrystalline cellulose | 70 mg/tablet |

For example, to produce 1000 L-oxiracetam capsules, the specific preparation method is: Raw materials were passed over 80 mesh sieve. The prescriptive amount of L-oxiracetam, lactose, microcrystalline cellulose, are taken and mixed to directly fill into capsules.

EXAMPLE 2

Raw material composition:

| (a) L-oxiracetam (99.6% of purity) | 200 mg/tablet |
| (b) Starch | 34 mg/tablet |
| (c) Microcrystalline cellulose | 60 mg/tablet |
| (d) Talcum powder | 6 mg/tablet |
| (e) 2% hydroxypropyl methyl cellulose (K4M model) | adequate amount |

For example, to produce 1000 L-oxiracetam tablets, the specific preparation method is: Raw materials were passed over 80 mesh sieve. The prescriptive amount of L-oxiracetam, starch, microcrystalline cellulose were taken and mixed homogenously, then added to soft material made by 2% HPMC solution. After granulating, drying, granulating,

TABLE 10

The effectd of L-oxiracetam, naloxone hydrochloride on traumatic coma on rat brain

| Groups | Number of animals | Dosage | Post-traumatic observation point (h) | | | | Remark |
| --- | --- | --- | --- | --- | --- | --- | --- |
| | | | 1 | 2 | 4 | 8 | |
| Control | 10 | 5 ml/kg | 5.8 ± 0.42 | 5.4 ± 0.52 | 4.8 ± 0.78 | 4.2 ± 1.01 | 2 dead |
| naloxone hydrochloride | 10 | 1 mg/kg | 4.4 ± 0.96** | 3.6 ± 0.84** | 3.0 ± 0 92** | 1.9 ± 0.88** | All survived |
| L-oxiracetam | 10 | 125 mg/kg | 5.1 ± 0.88* | 3.8 ± 0.78** | 3.0 ± 0.82** | 2.0 ± 0.67** | All survived |

Note:
*indicates comparing with control group $P < 0.05$
**indicates comparing with control group $P < 0.01$ The table above shows: model animals from brain damage after more than eight hours to score 4 points to maintain, and there is a 20% mortality in animals. To the left oxiracetam 125 mg/kg 1 hour Rat state began significantly improved mean score 5.1, and the control group were significantly different (P<0.05), and since then has shown a significant improvement in awareness of the effect, the entire experimental period There was no occurrence of an animal died, indicating left Oxiracetam traumatic coma effect on rat brain conclusive. Similarly positive drug naloxone hydrochloride the granules were added prescriptive amount of talcum powder and then mixing and tabletting.

EXAMPLE 3

Raw material composition:

| (a) L-oxiracetam (99.3% of purity) | 200 mg/tablet |
| (b) Lactose | 80.8 mg/tablet |

-continued

| | |
|---|---|
| (c) Sodium carboxymethyl starch | 72 mg/tablet |
| (d) Talcum powder | 7.2 mg/tablet |
| (e) 10% polyvinylpyrrolidone | adequate amount |

For example, to produce 1000 L-oxiracetam capsules, the specific preparation method is: Raw materials were passed over 80 mesh sieve. The prescriptive amount of L-oxiracetam, lactose, sodium carboxymethyl starch were taken and mixed homogenously, then added to soft material made by 10% PVP ethanol solution. After granulating, drying, granulating, the granules were added prescriptive amount of talcum powder and then mixing and filling into capsules.

What is claimed is:

1. A method for treating coma, comprising administering to a subject in need thereof a composition including an effective amount of levo-oxiracetam as an active ingredient, and pharmaceutical acceptable ingredients.

2. The method as claimed in claim 1, wherein the coma is induced by alcohol, anesthesia, or trauma.

3. The method as claimed in claim 1 or 2, wherein the composition including levo-oxiracetam is an injection or oral formulation.

4. The method as claimed in claim 1, 2 or 3, wherein the purity of levo-oxiracetam is more than 99.3%, based on the weight percentage.

5. A method for treating coma, comprising administering to a subject in need thereof a composition including an effective amount of oxiracetam as an active ingredient, and pharmaceutical acceptable ingredients.

6. The method as claimed in claim 5, wherein the coma is induced by alcohol, anesthesia, or trauma.

7. The method as claimed in claim 5 or 6, wherein the composition including oxiracetam is an injection or oral formulation.

* * * * *